United States Patent
Jang et al.

(10) Patent No.: US 10,945,516 B2
(45) Date of Patent: Mar. 16, 2021

(54) DEVICE MOUNTED ON MASK PACK, MASK PACK AND KIT COMPRISING THE SAME

(71) Applicant: BIOSENSOR LABORATORIES INC., Seoul (KR)

(72) Inventors: Myoung Hoon Jang, Seoul (KR); Joon Lee, Seoul (KR); Sung Koo Kang, Seoul (KR); Minwoong Jung, Seongnam-si (KR); Jihyun Lee, Seoul (KR)

(73) Assignee: BIOSENSOR LABORATORIES INC., Seoul (KR)

( * ) Notice: Subject to any disclaimer, the term of this patent is extended or adjusted under 35 U.S.C. 154(b) by 331 days.

(21) Appl. No.: 15/777,410

(22) PCT Filed: Jan. 5, 2017

(86) PCT No.: PCT/KR2017/000151
§ 371 (c)(1),
(2) Date: May 18, 2018

(87) PCT Pub. No.: WO2017/119742
PCT Pub. Date: Jul. 13, 2017

(65) Prior Publication Data
US 2018/0332951 A1     Nov. 22, 2018

(30) Foreign Application Priority Data

Jan. 5, 2016  (KR) .................. 10-2016-0000772
Jun. 10, 2016 (KR) .................. 10-2016-0072695
Jan. 5, 2017  (KR) .................. 10-2017-0001760

(51) Int. Cl.
*A45D 44/22*       (2006.01)
*A45D 44/00*       (2006.01)
(Continued)

(52) U.S. Cl.
CPC .......... *A45D 44/22* (2013.01); *A45D 44/002* (2013.01); *A61K 8/0212* (2013.01); *A61K 8/19* (2013.01);
(Continued)

(58) Field of Classification Search
CPC .. A45D 44/22; A45D 44/002; A45D 2200/25; A45D 2200/202;
(Continued)

(56) References Cited

U.S. PATENT DOCUMENTS 5,637,084 A      6/1997  Kontturi et al.
2009/0254018 A1 10/2009  Nakayama et al.

FOREIGN PATENT DOCUMENTS

EP   2857441 A1   4/2015
JP   7-504342 A   5/1995
(Continued)

OTHER PUBLICATIONS

Japanese Office Acction dated Jul. 16, 2019 in counterpart Japanese Patent Application No. 2018-536198 (4 pages in Japanese).
(Continued)

*Primary Examiner* — Mark Bockelman
(74) *Attorney, Agent, or Firm* — NSIP Law

(57) ABSTRACT

When a device mounted on a mask pack, and a mask pack and a kit including the device are used, the mask pack may be well attached onto an application site, for example, skin; delivery of a bioactive material via the skin may improve; and itching, pain, burning, and erythema that may occur during a process of delivering the bioactive material to the skin may be prevented by using the device including an electrode.

19 Claims, 10 Drawing Sheets

(51) Int. Cl.
| | |
|---|---|
| *A61K 8/02* | (2006.01) |
| *A61K 8/73* | (2006.01) |
| *A61K 8/65* | (2006.01) |
| *A61Q 19/02* | (2006.01) |
| *A61Q 19/08* | (2006.01) |
| *A61N 1/04* | (2006.01) |
| *H01M 8/22* | (2006.01) |
| *H01M 2/10* | (2006.01) |
| *A61N 1/00* | (2006.01) |
| *A61K 8/60* | (2006.01) |
| *A61K 8/67* | (2006.01) |
| *A61K 8/19* | (2006.01) |
| *A61K 8/64* | (2006.01) |

(52) U.S. Cl.
CPC ............... *A61K 8/602* (2013.01); *A61K 8/64* (2013.01); *A61K 8/65* (2013.01); *A61K 8/671* (2013.01); *A61K 8/675* (2013.01); *A61K 8/73* (2013.01); *A61K 8/731* (2013.01); *A61N 1/00* (2013.01); *A61N 1/0436* (2013.01); *A61Q 19/02* (2013.01); *A61Q 19/08* (2013.01); *H01M 2/1022* (2013.01); *H01M 8/227* (2013.01); *A45D 2200/25* (2013.01); *H01M 2220/30* (2013.01); *H01M 2250/30* (2013.01)

(58) Field of Classification Search
CPC ........ A45D 2200/1027; H01M 2/1022; H01M 8/227; H01M 2250/30; H01M 2220/30; A61N 1/00; A61N 1/0436; A61N 1/0428; A61N 1/0444; A61K 8/602; A61K 8/671; A61K 8/675; A61K 8/19; A61K 8/64; A61K 8/0212; A61K 8/65; A61K 8/73; A61K 8/731; A61Q 19/02; A61Q 19/08; A61P 43/00; A61P 17/00; C07K 14/78; C08L 1/02

See application file for complete search history.

(56) References Cited

FOREIGN PATENT DOCUMENTS

| | | |
|---|---|---|
| JP | 2009-78828 A | 4/2009 |
| JP | 2009-256295 A | 11/2009 |
| JP | 2011-200679 A | 10/2011 |
| KR | 10-2007-0078184 A | 7/2007 |
| KR | 10-1511990 B1 | 4/2015 |

OTHER PUBLICATIONS

International Search Report dated Apr. 2017, in corresponding International Application No. PCT/KR2017/000151.

DEVICE MOUNTED ON MASK PACK, MASK PACK AND KIT COMPRISING THE SAME

CROSS REFERENCE TO RELATED APPLICATION(S)

This application is a U.S. National Stage Application of International Application No. PCT/KR2017/000151, filed on Jan. 5, 2017, which claims the benefit under 35 USC 119(a) and 365(b) of Korean Patent Application No. 10-2016-0000772, filed on Jan. 5, 2016, Korean Patent Application No. 10-2016-0072695, filed on Jun. 10, 2016, and Korean Patent Application No. 10-2017-0001760, filed on Jan. 5, 2017, in the Korean Intellectual Property Office.

TECHNICAL FIELD

One or more embodiments relate to a device mounted on a mask pack, and a mask pack and a kit including the device.

BACKGROUND ART

Generally, in the field of cosmetics, a sheet mask pack is a type of mask pack in which two sheets prepared in a face shape are attached so that a material does not need to be applied on a face using hands, and is a product that may result moisturizing and cleansing effects. Sheet mask packs on the market may have various forms such as a sheet having a design to cover the whole face, two sheets including one used in an upper part and the other in a lower part of a face, and sheets targeted to particular sites of a face such as under the eyes, around the eyes, and around the mouth.

Since a general mask pack delivers a bioactive material topically and percutaneously, delivery of effective materials to skin is limited. In order to deliver the effective materials to skin by using the mask pack, it may be important to make the mask pack attach well to the skin. Also, various attempts have been made to increase cosmetic effects, and one of them is using an iontophoresis device.

Iontophoresis is a method for delivering a drug which allows ionized molecules to easily penetrate into tissue. FIG. 1 is a schematic view of a conventional iontophoresis device. Referring to FIG. 1, the iontophoresis device is a technique for penetrating an ion material into skin by using a direct current. In order to use a repulsive force between ions having the same polarity, current is applied to a '+'electrode when an ion material having positive characteristics is used, and the current is applied to a '-'electrode when an ion material having negative characteristics is used, so that the ion material may easily penetrate into skin. Unlike a traditional method of percutaneous administration in which a drug is passively absorbed, the delivery may be active in an electrical field of the iontophoresis device.

However, the conventional iontophoresis device may have an oxidation reaction occur at a surface of the electrode attached onto the skin, and thus problems may occur such as itching, pain, burning, and erythema of the skin of a user using the iontophoresis device.

Therefore, there is a need to develop a mask pack that uses an iontophoresis principle to be well attached onto skin, efficiently delivers a material in the mask pack to the skin, and prevents itching, pain, burning, and erythema that may occur during a process of delivering a drug to skin by using an iontophoresis device including electrodes.

DETAILED DESCRIPTION OF THE INVENTION

Technical Problem

According to an embodiment, provided are a device mounted on a mask pack and a mask pack including the device, wherein the device and the mask pack allow the mask pack to be well attached onto skin, improve delivery of a bioactive material via skin, increase an amount of the bioactive material that is specifically being delivered to a desired site, for example, a site where there are many wrinkles, and prevent side reactions that may occur during a process of delivering an active material to skin by using a battery including an electrode. Technical problems aimed to be resolved by the embodiment of are not limited to technical problems described herein, and other technical problems may be inferred from other embodiments hereinafter.

Technical Solution

According to an embodiment, a device mounted on a mask pack includes a battery unit having a negative electrode and a positive electrode; and an intermediate sheet that is electrically connected to the battery unit, wherein the intermediate sheet is configured such that a current generated from the battery unit flows through a material-containing sheet of the mask pack.

According to another embodiment, a mask pack includes the device; and the material-containing sheet that is connected to a surface opposite to a surface at which the intermediate sheet of the device is connected to the battery unit.

According to another embodiment, a kit includes the device or the mask pack; and a container including an aqueous solution for activating the device.

Advantageous Effects of the Invention

According to an embodiment, when a device mounted on a mask pack and a mask pack and a kit including the device are used, the mask pack may be well attached onto an application site, for example, skin; delivery of a bioactive material via skin may improve; and itching, pain, burning, and erythema that may occurred during a process of delivering the bioactive material to skin may be prevented by using the device including an electrode.

DESCRIPTION OF THE DRAWINGS

FIG. 7 is a schematic view illustrating an activation principle of the mask pack using a reverse electrodialysis battery, according to another embodiment;

BEST MODE

The terms used in this specification are those general terms currently widely used in the art in consideration of functions in regard to the inventive concept, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

As used herein, the terms "comprise" or "include" should not be understood as necessarily include all of various elements or several steps described in the specification, but the term should be understood as not including some of the elements or some of the steps, or further including additional elements or steps.

Also, the terms such as "first", "second", etc. including an ordinal number may be used herein to describe various components, but the components should not be limited by the terms. These terms are only used to distinguish one component from another.

The description of embodiments below should not be understood as limiting the scope of the inventive concept, and anything that would have been easily inferred by those of ordinary skill in the art needs to be understood as that belongs to the scope of these embodiments. Hereinafter, embodiments for illustration only will be described by referring to the attached drawings.

According to an embodiment, provided is a device mounted on a mask pack.

Figure 1:
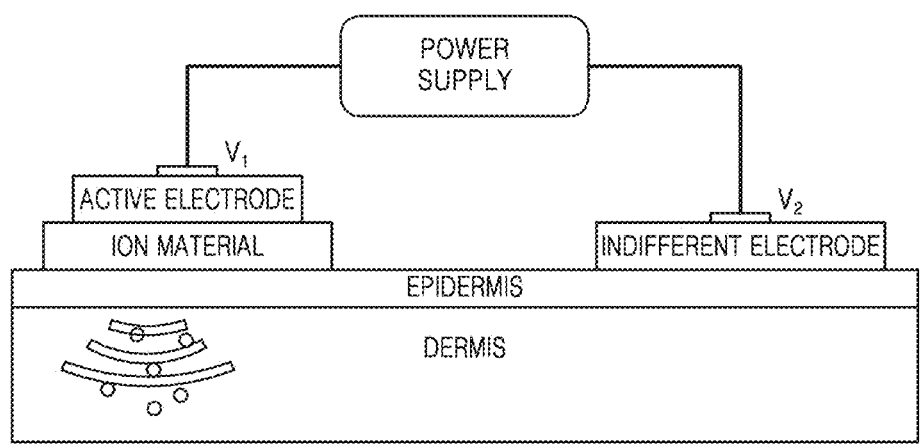
FIG. 1 is a schematic view of a conventional iontophoresis device.
Figure 2:
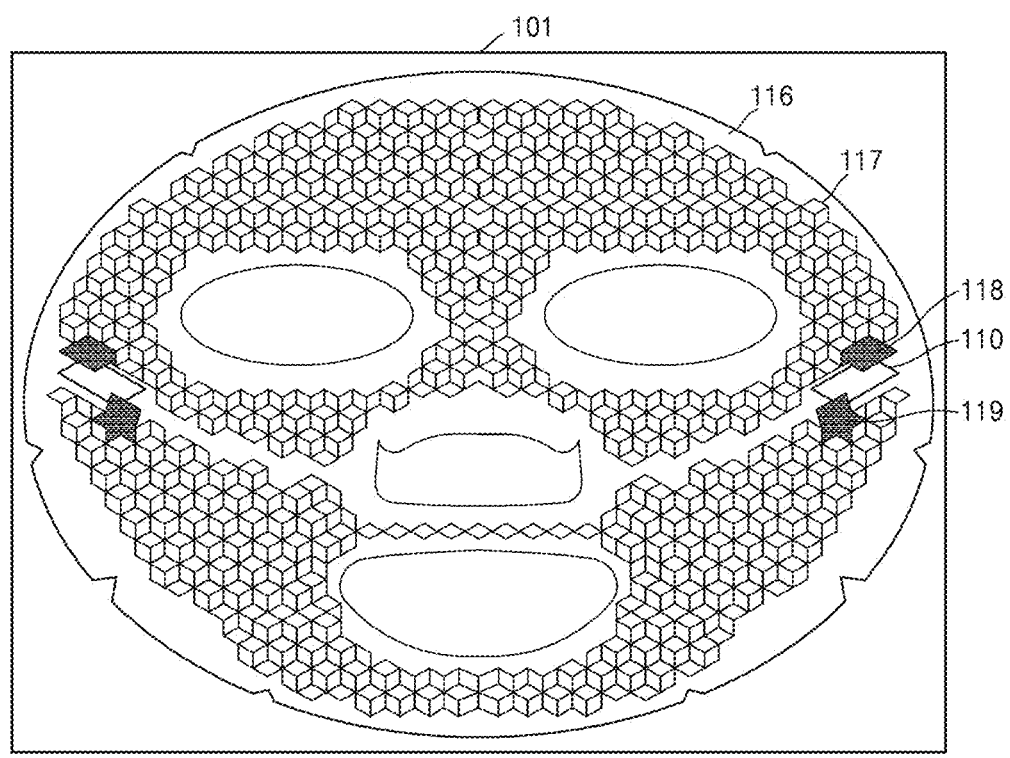
FIG. 2 is a schematic view of a device mounted on a mask pack, according to an embodiment.

FIG. 2 is a schematic view of a device 101 mounted on a mask pack, according to an embodiment.

Referring to FIG. 2, the device 101 mounted on a mask pack includes a battery unit 110 that has a negative electrode and a positive electrode; and an intermediate sheet 116 that is electrically connected with the battery unit 110.

In one embodiment, the battery unit 110 may be any battery that is capable of generating a current. For example, the battery unit 110 may include a reverse electrodialysis battery, a primary battery, or a secondary battery, and, in particular, the battery unit 110 may include at least one battery selected from the group consisting of a flexible battery, an alkali battery, a dry battery, a mercury battery, a lithium battery, a nickel-cadmium battery, a nickel-hydrogen battery, a lithium ion secondary battery, and a lithium ion polymer secondary battery. The reverse electrodialysis battery will be described in detail by referring to FIGS. 6 and 7. The battery unit 110 may be positioned on any part of a surface of the intermediate sheet 116.

The battery unit 110 may include electrodes, and the electrodes, that is, a negative electrode 131 and a positive electrode 132, may be electrically connected to the intermediate sheet 116 by connection units 118 and 119 of the intermediate sheet 116. A material that may be used in the electrodes may include a conductive material, and an example of the material may be silver, silver epoxy, palladium, copper, aluminum, gold, titanium, chrome, nickel, platinum, silver/silver chloride, silver/silver ion, or mercury/mercury oxide.

In one embodiment, the intermediate sheet 116 may be configured such that a current generated from the battery unit 110 flows through a material-containing sheet 120 of the mask pack. The intermediate sheet 116 may partially include an insulating site, and a current generated by the negative electrode 131 and the positive electrode 132 of the battery may not be electrically connected due to the insulating site of the intermediate sheet 116. For example, the intermediate sheet 116 may be partially coated or printed in a mesh structure formed of a conductive material 117 to form a circuit. The circuit may include two separate circuits, wherein one of the circuits is connected to the positive electrode 132, and the other may be connected to the negative electrode 131. The circuits formed by the conductive material 117 may also not be electrically or physically connected. For example, the mask pack or a philtrum site or a chin site of the device 101 mounted on a mask pack may not be physically connected, and thus the circuits formed by the conductive material 117 may not be connected. In this regard, the flow of the current of the mask pack according to an embodiment may improve, and thus an increased amount of materials may be delivered throughout the mask pack.

Thus, the intermediate sheet 116 may include a conductive material at least in a portion of the intermediate sheet 116, may be coated with a conductive material, or may be formed of a woven or non-woven conductive material (e.g., non-woven fabric). Also, for example, the intermediate sheet 116 may have a dry form. Also, a material of the intermediate sheet 116 may include a synthetic resin, for example, an acryl resin, a urethane resin, a silicon resin, a styrene resin, an aniline resin, an amino resin, an aminoalkyd resin, a vinyl acetate resin, an alkyd resin, an epoxy resin, a toluene resin, or a combination thereof. The conductive material may be selected from the group consisting of carbon, gold, silver, aluminum, copper, steel use stainless (SUS), and a combination thereof. For the coating with the conductive material, the conductive material may include at least one paste selected from the group consisting of a carbon paste, a gold paste, a silver paste, an aluminum paste, a copper paste, an SUS paste, and a combination thereof. The coating or printing with the conductive material may be performed by using a method that is obvious to those of ordinary skill in the art, and, for example, the coating may be performed by using techniques such as gravure printing, offset printing, digital printing, or transfer printing. Those of ordinary skill in the art may determine an appropriate technique and an amount of the paste that is being printed on the intermediate sheet 116 to obtain a desired conductivity value.

Also, the intermediate sheet 116 may further include the connection units 118 and 119 so as to be electrically connected with the battery unit 110. The connection units 118 and 119 may be formed of the same material as the conductive material 117.

In one embodiment, the intermediate sheet 116 may allow the current generated from the battery unit 110 to flow into the material-containing sheet 120. The intermediate sheet 116 may be disposed on a site of interest of a face to deliver a material when the mask pack is applied onto the face. For example, although the mask pack is applied to the whole face since the material to be delivered to an object is applied to the whole material-containing sheet 120, a material in the mask pack may be well delivered by locating the intermediate sheet 116 at a particular site of the face, for example, a site at which there are many wrinkles or a site at which there is much acne. Those of ordinary skill in the art may appropriately determine a size and a shape of the intermediate sheet 116 so that the material may be well delivered to the site of interest of the face.

The intermediate sheet 116 may have a circuit that is formed such that a current generated from the battery unit 110 may flow throughout the whole application site, and, for example, a conductivity of the intermediate sheet 116 may be in a range of 0.1 ohm/cm to 10 ohm/cm. In particular, the conductivity may be 10 ohm/cm or less, 8 ohm/cm or less, 6 ohm/cm or less, 4 ohm/cm or less, 2 ohm/cm or less, or 1 ohm/cm or less.

In one embodiment, a mask sheet directly contacting skin may be pressed due to the existence of the intermediate sheet 116 coated by the conductive material, and thus the mask pack may be well attached onto skin.

Also, since the mask pack delivers a bioactive material to skin by using a battery including electrodes, delivery of a material may increase, and the mask pack according to an embodiment may prevent a side effect that may be caused during the process of delivering a material.

In another embodiment, the number of the battery unit 110 in the device 101 may be one or two. When the number of the battery unit 110 is two, the battery units 110 may be disposed on the same surface of the intermediate sheet 116. Also, the positive electrode 132 of each of the two battery units 110 may be electrically connected by the conductive part 117 of the intermediate sheet 116, and the negative electrode 131 of each of the two battery units 110 may be also electrically connected by the conductive part 117 (e.g., a part coated with a conductive material) of the intermediate sheet 116. Also, as described above, the positive electrode 132 and the negative electrode 131 of each of the two battery units 110 may not be electrically connected to a current generated from the negative electrode 131 and the positive electrode 132 of the battery unit 110 due to the insulating site (e.g., a part that is not coated with a conductive material) of the intermediate sheet 116.

According to another embodiment, provided is a mask pack including the device 101.

Figure 3:
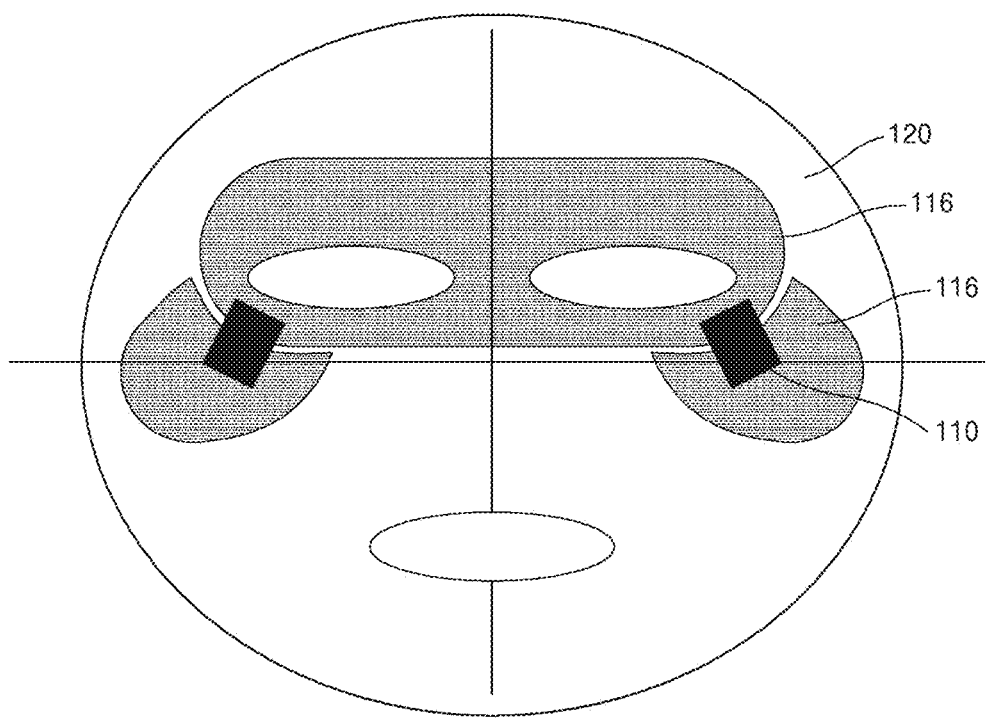
FIG. 3 is a schematic view of a top surface of the mask pack, according to an embodiment.
Figure 4:
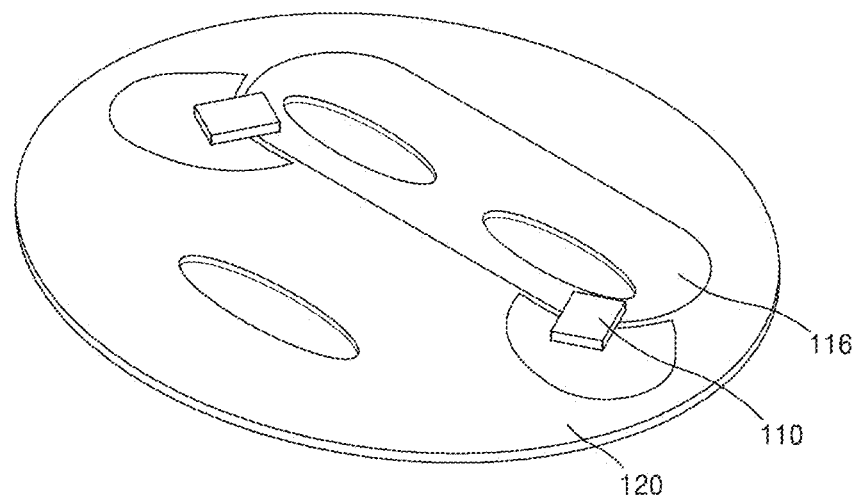
FIG. 4 is a schematic perspective view of the mask pack, according to an embodiment.
Figure 5:
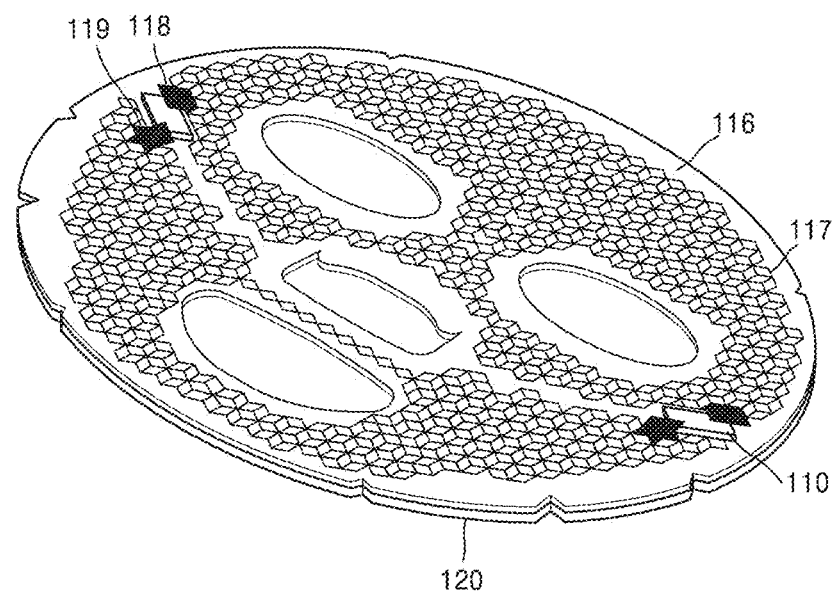
FIG. 5 is a schematic perspective view of a mask pack, according to another embodiment.

Referring to FIGS. 3 to 5, the mask pack may include the device 101; and a material-containing sheet 120 that is connected to a surface opposite to a surface at which an intermediate sheet 116 is connected to a battery unit 110.

The device 101 is the same as described herein.

In one embodiment, the mask pack may include the battery unit 110 that has a positive electrode and a negative electrode; the intermediate sheet 116 that is electrically connected to each of the positive electrode and the negative electrode of the battery unit 110; and one or two of a first or second material-containing sheet 120 connected to one surface of the two intermediate sheets 116 or one surface of each of the two intermediate sheets 116; and may be configured such that a current generated from the battery unit 110 flows throughout the material-containing sheet 120. Also, the material-containing sheet 120 may be configured such that a material in the material-containing sheet 120 may be delivered to an object by a current generated from the battery unit 110. Also, the material-containing sheet 120 may be connected to a surface on which the conductive material 117 is printed, and the material-containing sheet 120 may be connected to a surface opposite to a surface on which the conductive material 117 is printed. Regarding the first or second material-containing sheet 120, a material to be delivered to an object may be included in both the first and second material-containing sheets 120, or a material to be delivered to an object may be only included in the first material-containing sheet 120. Also, the material-containing sheet 120 may have a wet form. The material-containing sheet 120 may be configured such that the material to be delivered to an object is included in an electrolyte solution, essence, hydrogel, cellulose, agarpse, gelatin, or collagen. For example, when the material-containing sheet 120 includes cellulose, the mask pack may be a cellulose pack, and when the material-containing sheet 120 includes collagen, the mask pack may be a collagen pack. The cellulose pack and the mask pack used herein have meanings generally known in the art. Thus, the material-containing sheet 120 may denote a sheet that is generally used as a conventional mask pack. The material-containing sheet 120 may also include an electrolyte, and examples of the electrolyte may include NaCl, $MgCl_2$, AgCl, $CuCl_2$, $CaCl_2$), and a combination thereof. A concentration of the electrolyte included in the material-containing sheet 120 may be, for example, in a range of about 0.01% to about 0.2%, about 0.02% to about 0.18%, about 0.05% to about 0.18%, about 0.08% to about 0.15%, about 0.08% to about 0.12%, about 0.08%, about 0.09%, about 0.1%, or about 1.1%. When the electrolyte is included in the material-containing sheet 120 at this low concentration, the material-containing sheet 120 may have appropriate conductivity while not deteriorating a feeling when using the material-containing sheet 120, and thus a material in the material-containing sheet 120 may be well delivered to the application site. Also, the material-containing sheet 120 may further include water-soluble polysaccharides, for example, arabio galactan. When the material-containing sheet 120 includes water-soluble polysaccharides, the conductivity thereof may further increase.

Also, the material-containing sheet 120 may include a material having a charge or a polarity. The material may be a material to be delivered to an object. The material-containing sheet 120 may be provided with the material to be delivered to an object contained therein, or the material to be delivered to an object may be provided by being contained in a separate container in the form of a kit while the material-containing sheet 120 does not include the material to be delivered to an object.

Also, for example, the material-containing sheet 120 may include an aqueous solution or a buffer solution including or containing a material having a charge or a polarity; or a hydrogel or a matrix. The material included in the material-containing sheet 120 may be mixed with an enhancer that promotes delivery of the material. The enhancer may be roughly classified into an enzymatic enhancer and a non-enzymatic enhancer. Examples of the enzymatic enhancer may include enhancers using a proteolytic enzyme such as papain, trypsin, pepsin, and bromelain, and examples of the non-enzymatic enhancer may include enhancers using non-enzymatic materials such as lactam compounds, ethyl acetate, ethyl alcohol, dioxolane, nonionic surfactants, propyleneglycol, caprylic acid, capric triglyceride, and n-decyl-methylsulfoxide. The enhancers may be appropriately mixed and used according to the material to be delivered. Also, the matrix material may include esters of acrylic acid or methacrylic acid and an acryl or methacryl resin such as a polymer of an alcohol. Examples of the alcohol may include butanol, pentanol, isopentanol, 2-methylbutanol, 3-methylpentanol, 2-ethylbutanol, isooctanol, decanol, or dodecanol. Also, examples of the polymer may include a copolymer with an ethylenically unsaturated monomer such as acrylic acid, methacrylic acid, acrylamide, methacrylamide, N-alkoxymethylacrylamide, N-alkoxymethylmethacrylamide, N-t-butyl acrylamide, itaconic acid, vinyl acetate, N-branched alkylmaleamate glycol diacrylate, or a mixture thereof. Other examples of the matrix material may include natural or synthetic rubber such as styrene-butadiene, butyl ether, neoprene, polyisobutylene, polybutadiene, and polyisoprene; cellulose derivatives such as polyvinyl acetate, urea formaldehyde resins, phenol formaldehyde resins, resorcinol formaldehyde resins, ethylcellulose, methylcellulose, nitrocellulose, cellulose acetate butyrate, and carboxymethylcellulose; and natural gums such as guar, acacia, pectin, starch, dextrin, albumin, gelatin, and casein. As is well known in the art, the materials may include a binder and a stabilizing agent. Also, examples of the object to which the material is delivered by the material-containing sheet 120 may include humans and mammals for different purposes.

The material having a charge or a polarity included in the material-containing sheet 120 may have a charge due to the material itself having a charge in an ion-conductive medium in the material-containing sheet 120 or may have a charge or a polarity due to solvation. The material having a charge or a polarity may include a physiologically active material or a drug. A molecular weight (MW) of the material may be, for example, in a range of about 100 to about 2000, about 200 to about 2000, about 300 to about 1000, about 300 to about 800, or about 400 to about 7000. Also, the material may include a whitening agent, an anti-wrinkle agent, a pharmaceutical agent, or a combination thereof. Examples of the whitening agent may include a *Broussonetia kazinoki* extract, niacinamide, adenosine, arbutin, ethyl ascorbyl ether, an oil-soluble licorice extract, ascorbyl glucoside, ascorbyl tetraisopalmitate, magnesium ascorbyl phosphate, alpha-bisabolol, or a combination thereof. Examples of the anti-wrinkle agent may include retinol, retinyl palmitate, adenosine, polyethoxylated retinamide, acetyl hexapeptide-3 or -8, acetyl octapeptide-3, acetyl tetrapeptide-5, palmitoyl pentapeptide, copper peptide, palmitoyl oligopeptide, palmitoyl dipeptide-10, palmitoyl tripeptide-1, palmitoyl tetrapeptide-7, palmitoyl pentapeptide-3, palmitoyl hexapeptide-12, pentapeptide-18 (Leuphasyl), or a combination thereof. Also, the material may be a protein. The protein may be a protein that is modified or ionized or in an ionizable form to be included in the material-containing sheet 120 and delivered.

Figure 6:
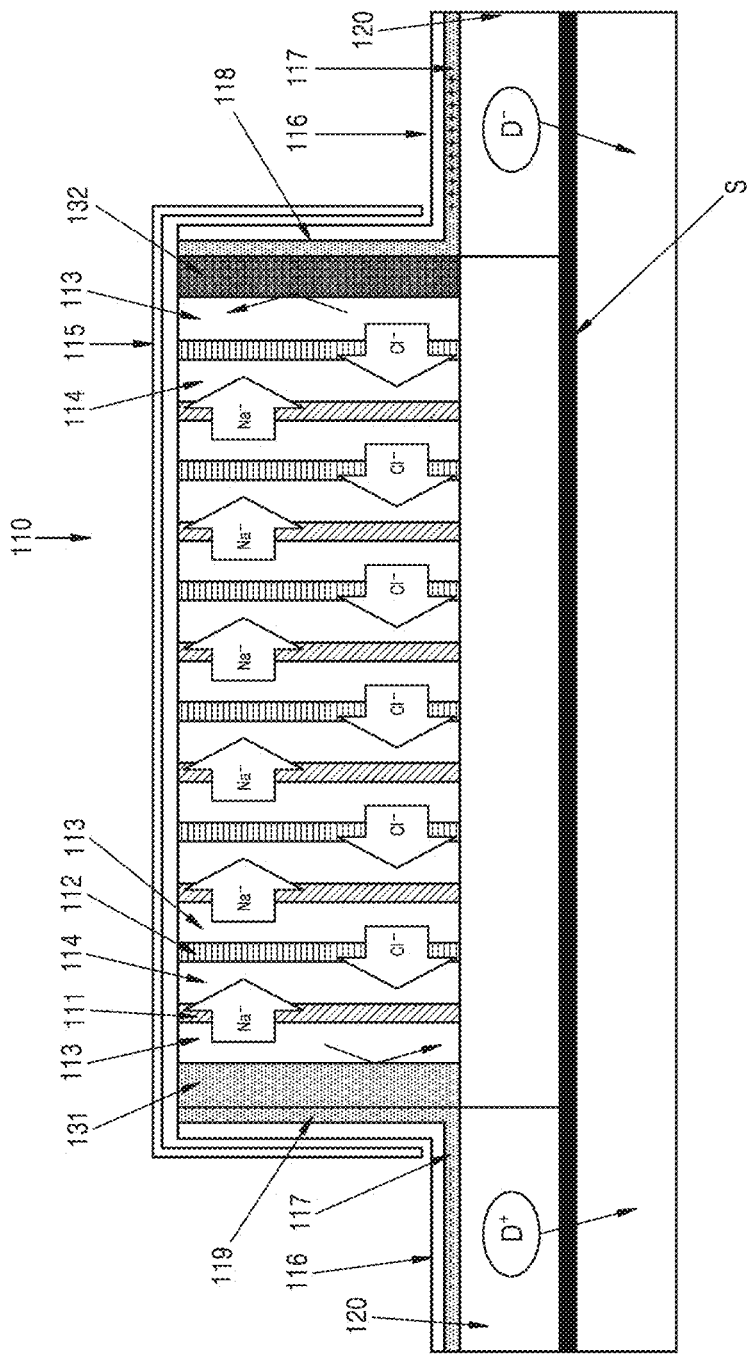
FIG. 6 is a schematic view of a side surface of the mask pack using a reverse electrodialysis battery, according to another embodiment.

An operation principle of the mask pack when the battery unit 110 is a reverse electrodialysis battery will be described with reference to FIGS. 6 and 7. The reverse electrodialysis battery 110 may include a cation exchange membrane 111; an anion exchange membrane 112 that is disposed apart from the cation exchange membrane 111; and chambers 113 and 114 that are at least partially defined with respect to the cation exchange membrane 111 and the anion exchange membrane 112 and contain an electrolyte between the cation exchange membrane 111 and the anion exchange membrane 112, wherein the cation exchange membrane 111 and the anion exchange membrane 112 are alternately arranged, and the chamber 113 that contains an electrolyte at a high concentration and the chamber 114 that contains an electrolyte at a low concentration alternately arranged.

The intermediate sheet 116 may be connected to electrode units 131 and 132 (electrode unit 131 is a negative electrode, and electrode unit 132 is a positive electrode) that exist on both outer surfaces of the reverse electrodialysis battery 110. The electrode unit 131 may be the negative electrode 131 when the chambers 113 and 114 (e.g., non-woven material) containing an electrolyte and the cation exchange membrane 111 exist on an outer surface, and the electrode unit 132 may be the positive electrode 132 when the chambers 113 and 114 (e.g, non-woven material) containing an electrolyte and the anion exchange membrane 112 exist on the outer surface. Here, as described below, electrons may be generated at the negative electrode 131 due to an oxidation reaction, and electrons may be consumed at the positive electrode 132 due to a reduction reaction.

(Negative electrode) $Ag \rightarrow Ag^- + e^-$ (Positive electrode) $AgCl + e^- \rightarrow Ag + Cl^-$ In one embodiment, a mask pack 100 may include a plurality of cation exchange membranes 111, a plurality of anion exchange membranes 112, and a plurality of chambers 113 and 114 containing an electrolyte, wherein the mask pack 100 has multiple layers, for example, in a range of 2 to 70 layers, 5 to 60 layers, 7 to 40 layers, 10 to 35 layers, or 15 to 30 layers, wherein the chambers 113 and 114 containing an electrolyte form one layer.

Since a surface of the material-containing sheet 120 may be in contact with an object S to which a material is administered, and a current generated from the reverse electrodialysis battery unit 110 may flow throughout the material-containing sheet 120 via the intermediate sheet 116, a material in the material-containing sheet 120 may be delivered to the object S. For example, cations ($Na^+$) in the chambers 113 containing the electrolyte at a high concentration penetrate through the cation exchange membranes 111 and migrate to the chambers 114 containing the electrolyte at a low concentration, and by a similar principle, anions ($Cl^-$) in the chambers 114 containing the electrolyte at a low concentration penetrate through the anion exchange membranes 112 and migrate to the chambers 114 containing the electrolyte at a low concentration. Migration of the ions occurs at all of the cation exchange membranes 111, the anion exchange membranes 112, and the chambers 113 and 114. As described above, electrons are generated at the negative electrode 131 by an oxidation reaction to supplement relative insufficiency of cations by using the migration of ions as an electromotive force, and electrons are consumed at the positive electrode 132 by a reduction reaction to supplement relative insufficiency of anions. Therefore, an ion current is generated in the reverse electrodialysis battery unit 110, and thus outputs a current.

Thereafter, a negative charge is charged at the conductive part 117 of the intermediate sheet 116 that is connected to the negative electrode 131 of the battery unit 110 through the connection unit 119, and thus a repulsive force may act on a cationic material $D^+$ included in the material-containing sheet 120. Similarly, a positive charge is charged at the conductive part 117 of the intermediate sheet 116 that is connected to the positive electrode 132 of the battery unit 110 through the connection unit 118, and thus a repulsive force may act on an anionic material $D^-$ included in the material-containing sheet 120. Thus, for example, when the material-containing sheet 120 is connected to the negative electrode 131 of the battery unit 110, the cations $D^+$ may penetrate (be delivered) through skin to an object, and when the material-containing sheet 120 is connected to the positive electrode 132 of the battery unit 110, the anions $D^-$ may penetrate (be delivered) through skin to an object.

Also, a voltage or a current generated from the reverse electrodialysis battery unit 110 may be changed by controlling types or thicknesses of the cation exchange membrane 111 and the anion exchange membrane 112 or volumes of the chambers 113 and 114. Regarding thicknesses that determine volumes of the chambers 113 and 114 containing an electrolyte, thicknesses of the chambers 113 and 114 positioned at a middle portion of the battery unit 110 may be thicker than those of the chambers 113 and 114 positioned at an outer portion of the battery unit 110. In this regard, a voltage or a current output from the battery unit 110 may increase. A range of the voltage output from the battery unit 110 may be at least about 0.5 volts or higher, or, for example, in a range of about 0.5 volts to about 15 volts, about 1.0 volts to about 10 volts, about 1.5 volts to about 8.0 volts, about 2.0 volts to about 6.0 volts, about 2.0 volts to about 4.0 volts, or about 2.0 volts to about 3 volts. A range of the current output from the battery unit 110 may be at least about 0.1 mA or higher, or, for example, in a range of about 0.1 mA to about 10 mA, about 0.2 mA to about 8 mA, about 0.4 mA to about 6 mA, about 0.5 mA to about 4 mA, about 0.5 mA to about 2 mA, or about 0.5 mA to about 1 mA. The current may be different according to skin resistance, and the skin resistance may be in a range of about 1000 to about 3000 Ohm.

As used herein, the term "reverse electrodialysis (RED)" may denote a salinity gradient energy that is generated by a difference in salt concentrations of two solutions and, in one embodiment, may refer to a phenomenon of allowing a current to flow through the mask pack 100. Therefore, the reverse electrodialysis battery unit 110 may denote a device generating a current by using reverse electrodialysis. For example, as used herein, the reverse electrodialysis battery unit 110 may generate a current by an ion concentration difference between electrolytes in a high-concentration electrolyte solution and a low-concentration electrolyte solution.

Also, since the mask pack 100 according to an embodiment uses reverse electrodialysis, the mask pack 100 may not require or have separate power or an electrode. For example, the battery unit 110 may be the only current source for delivering a material to an object. The mask pack 100 may be a current source for delivering a material to an object and may be formed of the battery unit 110 only, and the battery unit 110 may not have separate power or an electrode. In order to generate a current by the reverse electrodialysis, the battery unit 110 may use an electrolyte solution. As used herein, the term "electrolyte" may refer to a material that is dissociated into ions in a solvent such as water to allow a current to flow, and the electrolyte solution may denote a solution such as water in which an electrolyte is dissolved. Thus, the electrolyte may be included in the electrolyte solution. The reverse electrodialysis battery unit 110 generates a current by using a difference between a high-concentration electrolyte solution and a low-concentration electrolyte solution, where an amount of an electrolyte in the chamber 113 including the electrolyte at a high concentration may be greater than an amount of an electrolyte in the chamber 114 including the electrolyte at a low concentration. The chamber 114 including the electrolyte at a low concentration may include a chamber that does not contain an electrolyte. For example, the electrolyte may be included in an electrolyte solution, and the chamber 113 containing the electrolyte at a high concentration may include an electrolyte solution of an ion concentration in a range of about 0.1 to about 20 mol/L, or, for example, about 0.7 to about 10 mol/L, about 1.0 to about 8.0 mol/L, about 1.0 to about 2.0 mol/L, or about 1.2 to about 1.8 mol/L, and the chamber 114 containing the electrolyte at a low concentration may not include an electrolyte or may include an electrolyte solution of an ion concentration in a range of about 0.005 to about 10 mol/L, or, for example, about 0.005 to about 8 mol/L, about 0.01 to about 6 mol/L, about 0.05 to about 6.0 mol/L, about 0.1 to about 4.0 mol/L, or about 0.1 to about 2.0 mol/L. The ion concentration of the electrolyte solution in the chamber 113 containing the electrolyte at a high concentration may be higher than the ion concentration of the electrolyte solution in the chamber 114 containing the electrolyte at a low concentration.

In another embodiment, the chambers 113 and 114 including the electrolyte may include electrolyte paste. The electrolyte paste may include a water-soluble polymer binder and an electrolyte. The water-soluble polymer binder may be, for example, at least one selected from the group consisting of a cellulose-based resin, xanthan gum, polyvinyl pyrrolidone, polyvinyl alcohol, a water-soluble (meth) acryl resin, polyether-polyol, and polyether-urea-polyurethane. When the electrolyte paste is prepared by mixing the water-soluble polymer binder and the electrolyte, a chamber including the electrolyte paste may be prepared. When the electrolyte paste is used as an electrolyte included in the chamber, resistance may decrease, which may facilitate migration of the electrolyte in the chamber.

In another embodiment, the chambers 113 and 114 including the electrolyte may contain a hydrogel including an electrolyte. For example, the chamber 113 containing the electrolyte at a high concentration may contain a solid material including the electrolyte at a high concentration or a hydrogel including the electrolyte at a high concentration, or the chamber 114 containing the electrolyte at a low concentration may be empty or may contain a solid material including the electrolyte at a low concentration or a hydrogel including the electrolyte at a low concentration. When the solid material or the hydrogel is included, for example, when a salt (NaCl) in a solid state is included, the solid material or the hydrogel is dissolved in water as the water flows into the chamber and forms an aqueous electrolyte solution, which may generate a flow of ions. The solid material or the hydrogel may be any material that has water-solubility or permeability of an ionic material and has appropriate mechanical characteristics. Examples of the solid material or the hydrogel may include agar, polyethylene glycoldiacrylate (PEGDA), poly(2-hydroxyethyl methacrylate) (PHEMA), and an alginic acid such as sodium alginate, calcium alginate, or potassium alginate. Also, the solid material or the hydrogel may include a solid powder preparation of an ionic binding material.

The chambers 113 and 114 containing an electrolyte may have a woven or non-woven form, and may be capable of absorbing an aqueous solution. For example, the non-woven form may be non-woven fabric. When the chambers 113 and 114 containing an electrolyte have a woven form and are capable of absorbing an aqueous solution, the electrolyte may be included in the chambers in the form of a powder. When the electrolyte exists in the form of a powder in the chambers of a woven form, a solution, for example the electrolyte, is dissolved in water as the water flows into the chambers, thus forming an aqueous electrolyte solution such that a flow of ions may occur. Also, the chambers 113 and 114 may be woven or non-woven material impregnated with an electrolyte. The woven or non-woven material impregnated with an electrolyte may be prepared by, for example, adding non-woven material into a NaCl solution and performing a hot-air rolling process thereon. For example, the chamber 113 containing the electrolyte at a high concentration may be prepared by adding woven or non-woven material capable of absorbing an aqueous solution to a high-concentration NaCl solution and performing a hot-air rolling process thereon, and the chamber 114 including the electrolyte at a low concentration may be prepared by adding woven or non-woven material capable of absorbing an aqueous solution to a low-concentration NaCl solution and performing a hot-air rolling process thereon. Also, the chamber 114 containing the electrolyte at a low concentration may be formed of woven or non-woven material that is capable of absorbing an aqueous solution but is not impregnated with NaCl.

During activation, amounts of the electrolytes or ion concentrations of the electrolyte solutions in the chamber 113 containing the electrolyte at a high concentration and the chamber 114 containing the electrolyte at a low concentration may be different from each other, such that a voltage of at least about 0.5 volts or higher, or, for example, in a range of about 0.1 to about 15 volts, about 0.2 to about 10 volts, about 1.0 to about 8.0 volts, about 2.0 to about 6.0 volts, about 2.0 to about 4.0 volts, or about 2.0 to about 3 volts may be output. Also, amounts of the electrolytes or ion concentrations of the electrolyte solutions in the chamber 113 containing the electrolyte at a high concentration and the chamber 114 containing the electrolyte at a low concentration may be different from each other, such that a current of about 0.1 mA or higher, or, for example, in a range of about 0.1 to about 10 mA, about 0.2 to about 8 mA, about 0.4 to about 6 mA, about 0.5 to about 4 mA, about 0.5 to about 2 mA, or about 0.5 to about 1 mA, may be generated. Examples of the electrolyte may include NaCl, $MgCl_2$, AgCl, $CuCl_2$, $CaCl_2$), or a combination thereof.

As used herein, the term "ion-exchange membrane" may denote a membrane having a strong tendency to allow permeation therethrough of either cations or anions. The ion-exchange membrane may be a synthetic resin, and, for example, the synthetic resin may be cross-linked. Since the cation exchange membrane 111 has a negative charge, ions having a negative charge do not permeate therethrough as they are repelled by the cation exchange membrane 111, and only ions having a positive charge may permeate therethrough. For example, the cation exchange membrane 111 may be a cation exchange membrane having a sulfon group. On the other hand, the anion exchange membrane 112 has a positive charge, and thus ions having a positive charge do no permeate therethrough as they are repelled by the anion exchange membrane 112, and only ions having a negative charge may permeate therethrough. For example, the anion exchange membrane 112 may be an anion exchange membrane including tetravalent ammonium. Types of a monomer that forms the cation exchange membrane 111 may include 2-(meth)acrylamide-2-methylpropanesulfonic acid, 3-sulfopropane(meth)acrylate, 10-sulfodecane(meth)acrylate, and salts thereof; a carboxylic acid-type monomer, for example, 2-(meth)acryloylethylphthalic acid, 2-(meth)acryloylethylsuccinic acid, 2-(meth)acryloylethylmaleic acid, 2-(meth) acryloylethyl-2-hydroxyethylphthalic acid, 11-(meth)acryloyloxydecyl-1,1-dicarboxylic acid, and salts thereof; and a sulfuric acid-type monomer, for example, 2-(meth)acryloyloxyethyl dihydrogenphosphate, 2-(meth)acryloyloxyethyl phenyl hydrogenphosphate, 10-(meth)acryloyloxydecyl di hydrogenphosphate, 6-(meth)acryloyloxyhexyl dihydrogenphosphate, and salts thereof. Types of a monomer that forms the anion exchange membrane 112 may include N,N-dimethylaminoethyl(meth)acrylate, N,N-diethylaminoethyl(meth)acrylate, N,N-dimethylaminoethyl(meth)acrylate/methyl chloride, and N,N-diethylaminoethyl(meth)acrylate/methyl chloride. An ion exchange capacity (IEC) of the cation exchange membrane 111 or the anion exchange membrane 112 may be about 0.5 meg/g or higher or about 1.0 meg/g or higher, or, for example, in a range of about 0.5 to about 20.0 meg/g, about 1.0 to about 10.0 meg/g, about 2.0 to about 10.0 meg/g, or about 5.0 to about 10.0 meg/g. Also, permeation selectivity of the cation exchange membrane 111 or the anion exchange membrane 112 may be about 70% or about 80% or higher, or, for example, in a range of about 80 to about 100%, about 90 to about 100%, or about 95 to about 100%.

In one embodiment, the mask pack 100 may further include a spacer (not shown) to separate the cation exchange membrane 111 and the anion exchange membrane 112. The spacer may be the same as the chambers 113 and 114 containing an electrolyte. The spacer may prevent the ion exchange membranes from being attached to each other and may include, for example, a net structure formed of polypropylene or polyethylene; sponge; tape; a woven material, for example, fabric; or a non-woven material. Also, the spacer may serve as a support that supports the cation exchange membrane 111, the anion exchange membrane 112, and the chambers 113 and 114 containing an electrolyte. The support may be, for example, a gasket.

Figure 9:
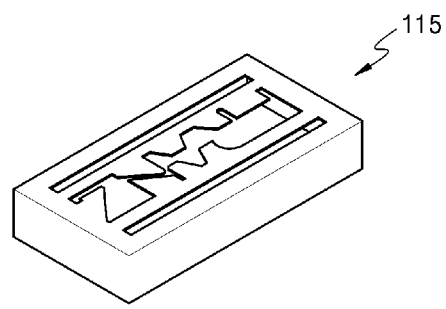
FIG. 9 is a view that illustrates a container of a battery unit of the device mounted on a mask pack prepared according to an example.

Also, as shown in FIG. 9, the reverse electrodialysis battery unit 110 may further include a container 115 for accommodating the reverse electrodialysis battery unit 110. The container 115 may include a hole for administering a solution for activating the reverse electrodialysis battery unit 110 or may be configured to expose a portion of the reverse electrodialysis battery unit 110. A plurality of holes of the container 115 may be formed in a length direction of the container 115. The length direction may refer to a direction parallel to exchange membranes of the reverse electrodialysis battery unit 110. Additional holes may be appropriately selected and formed by those of ordinary skill in the art. The container 115 may maintain and support elements in the reverse electrodialysis battery unit 110. Also, for example, the container 115 may be configured such that a solution in the chambers 113 and 114 may not leak. Also, a portion of the container 115 may serve as a spacer (not shown), for example, by using double-sided tape, in addition to the spacer described above. Also, the container 115 may be an insulator, and a material of the container 115 may be any material conventionally used as an insulator. Examples of the material may include cellophane, cellulose acetate, ethylcellulose, plasticized vinyl acetate-vinyl chloride copolymers, polyethylene terephthalate, nylon, polyethylene, polypropylene, polyvinylidene chloride, rubber strings, soft plastics, hard plastics, metal plates, wooden plates, paper, cloth, and aluminum foil.

Figure 7A:
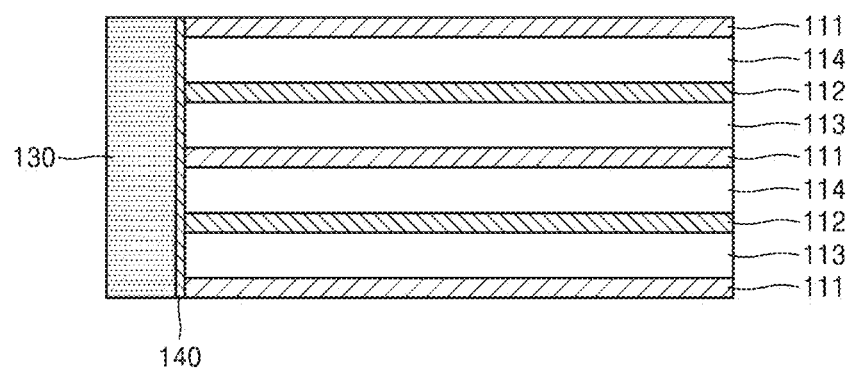
FIG. 7A shows an electrolyte flow of the reverse electrodialysis battery before the activation.
Figure 7B:
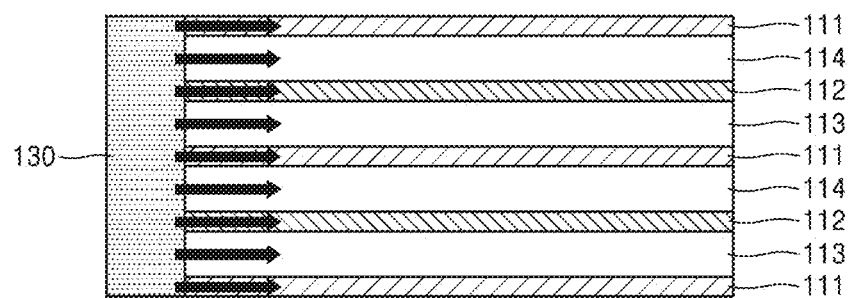
FIG. 7B shows an electrolyte flow of the reverse electrodialysis battery when the activation is started.
Figure 7C:
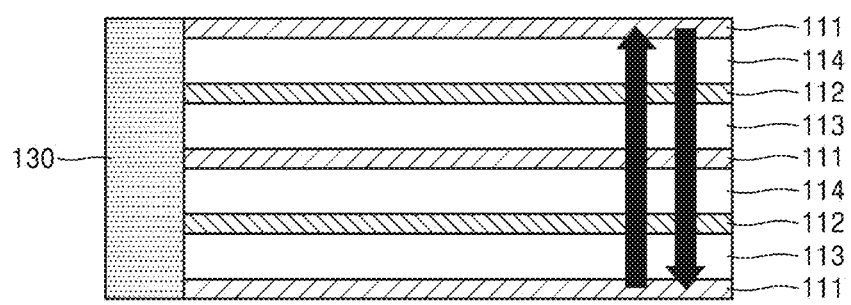
FIG. 7C shows an electrolyte flow of the reverse electrodialysis battery after the activation.

FIG. 7 illustrates an example of a reverse electrodialysis battery that is being activated. In the reverse electrodialysis battery according to an embodiment, as shown in FIG. 7A, a water-permeable membrane 140 may be disposed on at least a portion of a side-wall located between the cation exchange membrane 111 and the anion exchange membrane 112 as a side-wall of the chambers 113 and 114. Also, a water supply unit 130 that supplies water to the chambers 113 and 114 may be connected to at least one portion of the side-wall of the chambers 113 and 114. The water supply unit 130 and the chambers 113 and 114 may fluidically communicate via a flow path or a channel (not shown). A means or a valve for controlling the fluidic communication may be further included in the reverse electrodialysis battery. The side-wall used herein may denote a surface that is not a surface facing the chambers 113 and 114. Subsequently, as shown in FIG. 7B, water in the water supply unit 130 may flow into the chambers 113 and 114 through the water-permeable membrane 140, and, in this regard, as shown in FIG. 7C, the flow of ions described above may occur. In addition to the water-permeable membrane 140 or the water supply unit 130, a device may be activated by an arbitrary means so as to generate an electrolyte ion concentration difference in the chambers 113 and 114 of the device. For example, the device may be activated by supplying water to the device for activation before and after a user applies the device onto skin.

According to another embodiment, provided is a kit including a device mounted on a mask pack or a mask pack including the device.

The kit may include a container that includes an aqueous solution (e.g., water) for activation of the device mounted on the mask pack. The aqueous solution may include an electrolyte. Also, the aqueous solution for activation may be a material having a viscosity or, for example, a hydrogel. The electrolyte is the same as described in relation to the electrolyte contained in the material-containing sheet 120.

The kit may further include a container containing a material to be delivered to an object. For example, the mask pack may be provided as a kit with a material contained in a particular container, while a material to be delivered to an object is not included. The material to be delivered to an object may be provided in a composition or a powder form. For example, the composition including the material may be provided in the form of cream, gel, liquid, essence, or serum. When the composition including the material has a certain viscosity or higher, and a user applies the material to the material-containing sheet, the material may be delivered into a body. Depending on a use, those of ordinary skill in the art may appropriately select a form of the drug being provided and features and components of the corresponding material-containing sheet. When the mask pack, the material, and/or the aqueous solution are provided as a kit, the user may apply the drug to the mask pack and activate the mask pack by using the aqueous solution to apply the mask pack on skin of the user or another person, and thus the material may be delivered into the body.

Figure 8:
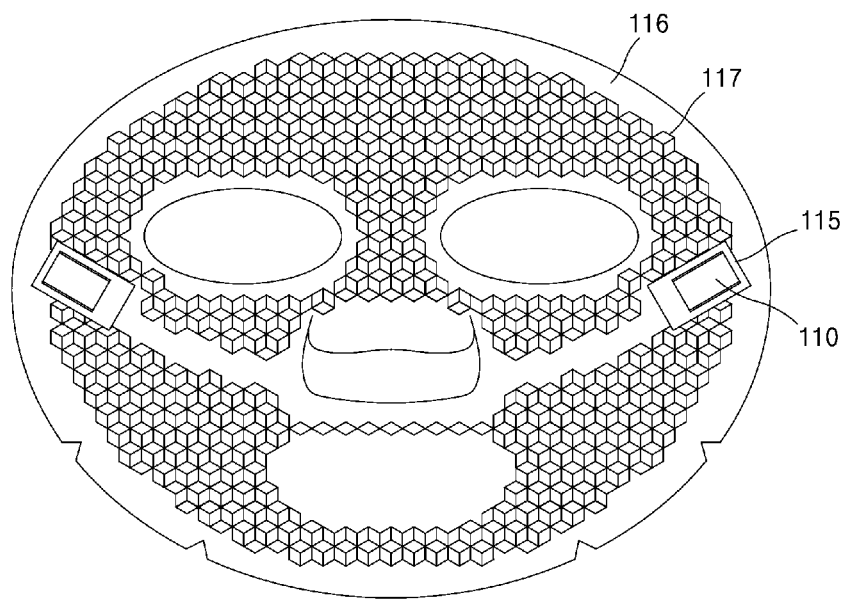
FIG. 8 is an image of a device mounted on a mask pack which is prepared according to an example.

FIG. 8 is an image of a device mounted on a mask pack prepared according to an embodiment. An intermediate sheet was non-woven, and 0.5 g of silver paste (available from Daejoo, Republic of Korea) was printed on the non-woven sheet. Ethylcarbitol acetate was used as a solvent to control viscosity. After printing the silver paste on the non-woven sheet, the non-woven sheet was heat-treated at 120° C. for 3 to 4 hours to remove solvents harmful to a human body, and cooling and deodorizing processes were simultaneously performed for 1 hour or more by an air-based process. Then, in order to perforate the intermediate sheet, a roll printed with the silver paste was marked so that the mark may be sensed during the perforating process so that the perforating was performed within an error range. A conductivity of the intermediate sheet thus obtained was about 1 ohm/cm. A battery unit used was a reverse electrodialysis battery. In particular, a non-woven material having a thickness in a range of about 0.2 to 0.5 mm was used as a chamber containing an electrolyte. A cation exchange membrane and an anion exchange membrane were purchased from ASAHI GLASS Co. SBX tape (available from CROSS) was used to prepare a spacer, a container, or a support to attach the non-woven material, the cation exchange membrane, and the anion exchange membrane. Holes were formed in the SBX tape for ion exchange, and thus a space for locating a solution in a chamber was secured. Also, NaCl powder of a certain amount was placed on the non-woven material so that a concentration of the chamber containing an electrolyte at a high concentration was 1.72 M, and a concentration of the chamber containing an electrolyte at a low concentration was 0.011 M. As described above, each portion of the reverse electrodialysis battery unit was prepared, and portions of the reverse electrodialysis battery unit were stacked in the order described above. The reverse electrodialysis battery unit having 31 layers was prepared, wherein one layer is formed of the chamber, and an area of the chamber was 1.5 cm×1.3 cm. Voltages and currents were measured by contacting a copper plate with the reverse electrodialysis battery unit and using a digital multimeter 34410A available from Keysight as a current meter.

The battery unit and the intermediate sheet were connected by using an ultrasound process. Insertion of the electrodialysis battery into the support (i.e., a container) was performed manually, and the battery unit was connected to the sheet. A lower portion of the support, and a portion of the intermediate sheet on which the silver paste was not printed were connected by using an ultrasound process, and an electrode of the battery, and a portion of the intermediate sheet on which the silver paste was printed were connected by using an ultrasound process.

The device mounted on a mask pack was prepared as described above, and the material-containing sheet, which was a microfibrous mask (available from PNC industry, Republic of Korea) of a wet form, was applied to skin. The aqueous solution for activating the mask pack was an aqueous solution including NaCl at a concentration of 0.1%.

Figure 10:
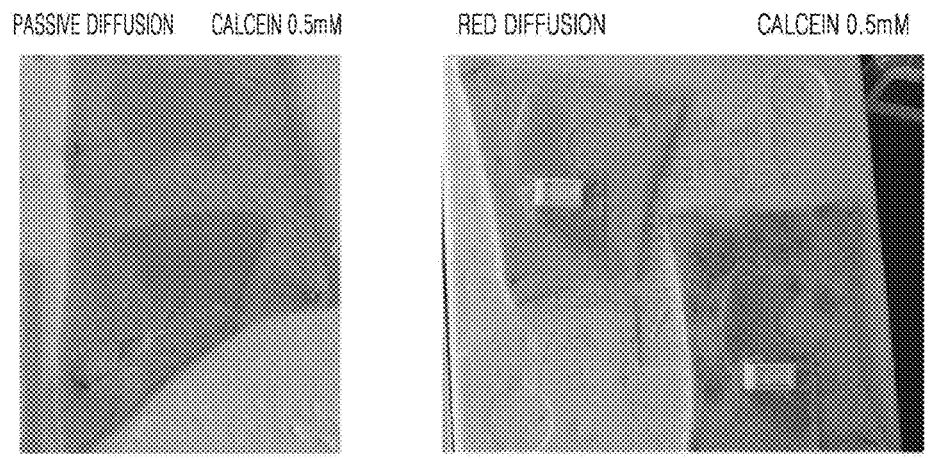
FIG. 10 is an image of the mask pack prepared according to an example applied to pig skin by dividing samples into a control group (left panel) and an experimental group (right panel)
Figure 11:
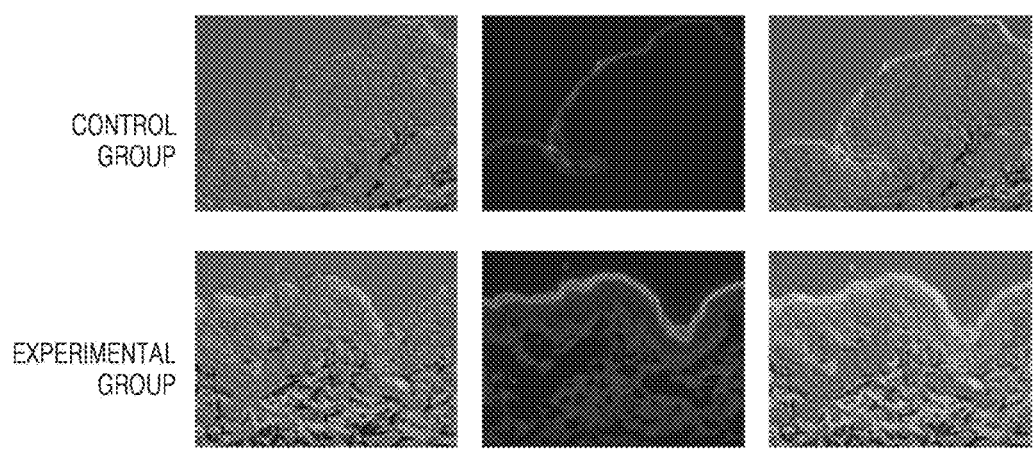
FIG. 11 is an image that illustrates a material delivery effect when the mask pack prepared according to an example is applied to pig skin.
Figure 12:
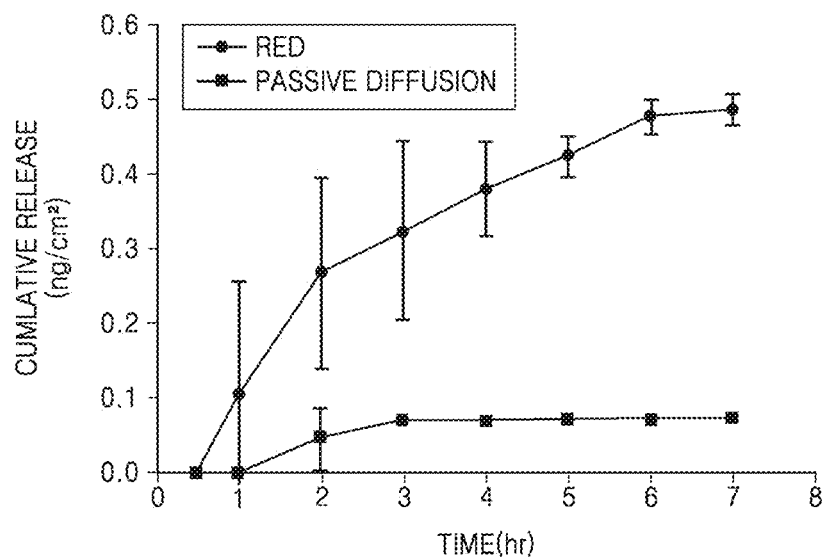
FIG. 12 is a graph that quantitatively illustrates a material delivery effect when the mask pack prepared according to an example is applied to pig skin.

As shown in FIGS. 10 and 11, whether the material was well delivered was tested by applying the mask pack onto pig skin. In particular, first, frozen pig skin purchased from a slaughterhouse was left out at room temperature and thawed for 2 to 3 hours for preparation. Then, hair on the pig skin was removed, and the pig skin was stretched to have elasticity and fixed on a plate with pins. As an experimental group, the mask pack prepared according to an embodiment was applied to the pig skin for 30 minutes, and as a control group, a mask pack on which a RED battery was not mounted was applied to the pig skin for 30 minutes. 0.5 mM of Calcein (having a molecular weight of 622.55 g/mol, available from Sigma-Aldrich), which is a fluorescent agent, was used in a material-containing portion. Thereafter, the pig skin was prepared as samples and fixed for 24 hours by using a fixing solution of 4% paraformaldehyde (pH 7.4 at 4° C.). After the fixing, the samples were sufficiently washed with a PBS (pH 7.4) solution, and embedded with a Tissue-Tek O.C.T. compound (available from Sakura Finetek, USA) and rapidly cooled. The cooled samples were cut to a size of 7 um by using a cryomicrotome (Shandon Cryotome SME Cryostat, Shandon Scientific LTD, Cheshire, England). The cryomicrotomed tissue was washed with a PBS solution, mounted on a mounting solution, covered with a cover slip, and observed using a fluorescent microscope (Axio Observer Z1; Zeiss, Gottingen, Germany), and the results are shown in FIG. 11. Also, fluorescence was quantified by using a spectrophotometer, and the results are shown in FIG. 12. As shown in FIGS. 11 and 12, fluorescence in the control group did not permeate the stratum corneum but remained, whereas the mask pack according to an embodiment deeply permeated below the stratum corneum. Also, as shown in FIG. 12, it was confirmed that, compared to an amount permeated into skin by passive diffusion (about 0.05 $ng/cm^2$), an amount of fluorescence of the mask pack that permeated into skin using reverse electrodialysis increased about 7 times (0.47 $ng/cm^2$).

Figure 13:
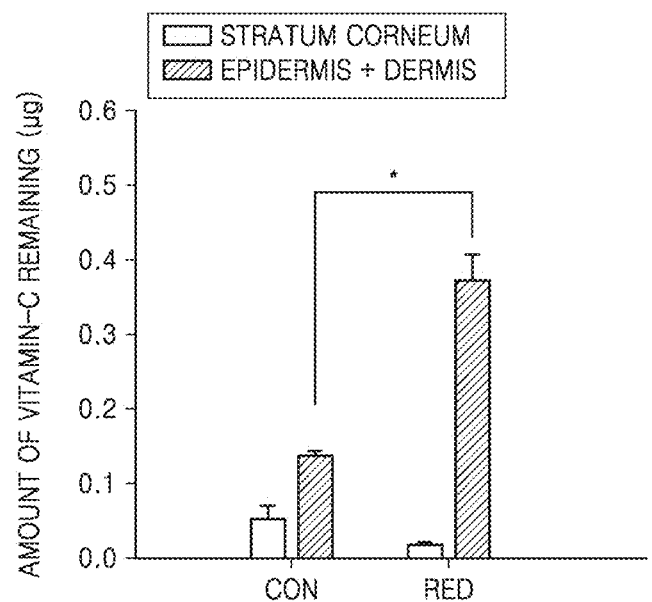
FIG. 13 is a graph that illustrates a vitamin C delivery effect when the mask pack prepared according to an example is applied to mouse skin.

Also, as shown in FIG. 13, a degree of absorption of vitamin C by skin of a mouse was evaluated. In particular, hairless mouse skin was used to measure a cumulative amount of vitamin C in skin of a mouse. As a control group, a preparation containing vitamin C in a general patch was used. As an experimental group, a preparation containing vitamin C in a patch using reverse electrodialysis was used. A cohesive hydrogel-type patch was prepared by using 3 w/v % Carbopol, and 0.5 mL of a vitamin C-containing cohesive hydrogel was loaded on the patch (an amount of vitamin C was 2.5 w/v %, and an amount of vitamin C loaded per patch was 12.5 mg). Back skin of a 5 week-old mouse (20 to 25 g) was taken, and the patch was mounted thereon. The patch was removed after being incubated for 6 hours, and the skin was carefully separated, quickly washed by using DDW and MeOH, and freeze-stored at −70° C. The frozen skin sample was thawed at room temperature, the stratum corneum was obtained therefrom by using 3M stripping cellophane tape, and the stratum corneum was moved to a 15 mL conical tube containing an extract solvent (a mixture including DW and MeOH at a ratio of 1:1). Next, the resultant was homogenized at 4000 rpm for 2 minutes by using a homogenizer to extract vitamin C from an epidermis layer and a dermis layer. Amounts of vitamin C in the samples were measured by using high-performance liquid chromatography (HPLC) using a mixture of acetonitrile and 0.3 M of $KH_2PO_4$ (pH 4) at a ratio of 40:60 as a mobile phase, a Nucleosil $NH_2$ (100 μm) column, a flow rate of 0.8 mL/min, an insertion volume of 20 μL, a UV wavelength of 264 nm, and a column temperature of 25° C., and the results are shown in FIG. 13. As shown in FIG. 13, in the case of the control group patch including vitamin C, locally remaining amounts of vitamin C of the epidermis layer and the dermis layer were small, but when the reverse electrodialysis patch according to an embodiment was used, locally remaining amounts of vitamin C of the epidermis layer and the dermis layer increased about 3 times relative to those of the control group.

As described above, it was confirmed that a mask pack prepared according to an embodiment was well attached onto skin and had improved delivery of a bioactive material through skin; and itching, pain, burning, and erythema that may occur during a process of delivering the bioactive material to the skin may be prevented by using a device including electrodes.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A device mounted on a mask pack, the device comprising:
    a reverse electrodialysis battery; and
    an intermediate sheet having an electrically conductive part,
    wherein the reverse electrodialysis battery comprises:
    a negative electrode and a positive electrode disposed at opposite ends of the reverse electrodialysis battery, and at least one of the electrodes electrically connected to the electrically conductive part of the intermediate sheet;
    a cation exchange membrane disposed between the negative electrode and the positive electrode;
    an anion exchange membrane disposed between the negative electrode and the positive electrode and spaced apart from the cation exchange membrane;
    a chamber that is at least partially defined with respect to the cation exchange membrane and the anion exchange membrane, contains an electrolyte, and absorbs an aqueous solution;
    wherein the reverse electrodialysis battery is activated when the aqueous solution is supplied into the chamber, and wherein the at least one electrode is made of a material that exchanges electrons with electrolyte ions to generate an electrical current deliverable to the conductive part.

2. The device of claim 1,
    wherein a plurality of the cation exchange membranes and a plurality of the anion exchange membranes are alternately arranged with each other so as to define a plurality of the chambers, and the plurality of the chambers comprise a plurality of first chambers comprising the electrolyte at a high concentration and a plurality of second chambers comprising the electrolyte at a low concentration that are alternately arranged with each other.

3. The device of claim 2, wherein the plurality of the chamber comprises 2 to 70 chambers.

4. The device of claim 2, wherein the intermediate sheet is connected to one of the plurality of the cation exchange membranes or one of the plurality of the anion exchange membranes that exists on an outer surface of the reverse electrodialysis battery.

5. The device of claim 2, further comprising a container for accommodating the reverse electrodialysis battery, wherein the container is configured such that a portion of the reverse electrodialysis battery is exposed for injection of a solution for activating the reverse electrodialysis battery.

6. The device of claim 2, wherein the electrolyte is comprised in an electrolyte solution, the plurality of the first chambers comprises the electrolyte solution having an ion concentration in a range of 0.1 to 20 mol/L, the plurality of the second chambers do not comprise the electrolyte or comprises the electrolyte solution having an ion concentration in a range of 0.005 to 10 mol/L, and the ion concentration in the plurality of the first chambers is higher than the ion concentration in the plurality of the second chambers.

7. The device of claim 1, wherein the intermediate sheet partially comprises an insulating site, and a current generated from the negative electrode and the positive electrode of the reverse electrodialysis battery is not electrically connected due to the insulating site of the intermediate sheet.

8. The device of claim 1, wherein the intermediate sheet comprises a conductive material in at least a portion of the intermediate sheet, is coated with a conductive material, or comprises a conductive woven or non-woven material.

9. The device of claim 8, wherein the conductive material is selected from the group consisting of carbon, gold, silver, aluminum, copper, steel use stainless (SUS), and a combination thereof.

10. The device of claim 8, wherein the conductive fabric or the conductive woven material comprises
- a first layer on a surface connected to a material-containing sheet of the mask pack and comprising a first synthetic resin;
- a second layer on the first layer and comprising the conductive material and a second synthetic resin;
- a third layer on the second layer and comprising the conductive material;
- a fourth layer on the third layer and comprising the conductive material and a third synthetic resin; and
- a fifth layer on the fourth layer and comprising a fourth synthetic resin.

11. The device of claim 1, wherein the chamber comprising the electrolyte comprises a woven or non-woven material capable of absorbing an aqueous solution.

12. The device of claim 11, wherein the woven or non-woven material is impregnated with the electrolyte.

13. The device of claim 1, wherein the electrolyte is at least one selected from the group consisting of NaCl, $MgCl_2$, AgCl, $CuCl_2$, $CaCl_2$), and a combination thereof.

14. A mask pack comprising:
the device of claim 1; and
a material-containing sheet that is connected to a surface opposite to a surface at which the intermediate sheet is connected to the reverse electrodialysis battery of the device.

15. The mask pack of claim 14, wherein the material-containing sheet is configured such that a material to be delivered to an object comprises an electrolyte solution, essence, a hydrogel, cellulose, agarose, gelatin, or collagen.

16. The mask pack of claim 14, wherein the material-containing sheet comprises a charge or a material having polarity.

17. The mask pack of claim 14, wherein the material is a whitening agent, an anti-wrinkle agent, a pharmaceutical agent, or a combination thereof.

18. The mask pack of claim 17, wherein the whitening agent is mulberry extract, niacinamide, adenosine, arbutin, ethyl ascorbyl ether, oil-soluble licorice extract, ascorbyl glucoside, magnesium ascorbyl phosphate, alpha-bisabolol, or a combination thereof.

19. The mask pack of claim 17, wherein the anti-wrinkle agent is retinyl palmitate, adenosine, polyethoxylated retinamide, acetyl hexapeptide-3 or -8, acetyl octapeptide-3, acetyl tetrapeptide-5, palmitoyl pentapeptide, copper peptide, palmitoyl oligopeptide, palmitoyl dipeptide-10, palmitoyl tripeptide-1, palmitoyl tetrapeptide-7, palmitoyl pentapeptide-3, palmitoyl hexapeptide-12, pentapeptide-18, leuphasyl, or a combination thereof.

* * * * *